: US009301711B2

(12) United States Patent
Bartol et al.

(10) Patent No.: US 9,301,711 B2
(45) Date of Patent: Apr. 5, 2016

(54) SYSTEM AND METHOD FOR ASSESSING NEURAL HEALTH

(71) Applicant: Innovative Surgical Solutions, LLC, Southfield, MI (US)

(72) Inventors: Stephen Bartol, Windsor (CA); Christopher Wybo, Highland, MI (US)

(73) Assignee: Innovative Surgical Solutions, LLC, Wixom, MI (US)

( * ) Notice: Subject to any disclaimer, the term of this patent is extended or adjusted under 35 U.S.C. 154(b) by 260 days.

(21) Appl. No.: 14/077,272

(22) Filed: Nov. 12, 2013

(65) Prior Publication Data

US 2014/0073986 A1 Mar. 13, 2014

Related U.S. Application Data

(63) Continuation-in-part of application No. 13/293,389, filed on Nov. 10, 2011, now Pat. No. 8,983,593.

(51) Int. Cl.
*A61B 5/05* (2006.01)
*A61B 5/11* (2006.01)
*A61B 5/00* (2006.01)
*A61N 1/05* (2006.01)

(52) U.S. Cl.
CPC .............. *A61B 5/11* (2013.01); *A61B 5/1104* (2013.01); *A61B 5/4041* (2013.01); *A61B 5/4519* (2013.01); *A61B 5/1107* (2013.01); *A61B 5/4029* (2013.01); *A61B 5/4893* (2013.01); *A61B 5/6828* (2013.01); *A61B 2505/05* (2013.01); *A61B 2562/0219* (2013.01); *A61N 1/0551* (2013.01)

(58) Field of Classification Search
CPC .. A61B 5/1104; A61B 5/1107; A61B 5/4029; A61B 5/4041; A61B 5/4893; A61B 2505/05; A61B 2562/0219
See application file for complete search history.

(56) References Cited

U.S. PATENT DOCUMENTS 3,200,814 A 8/1965 Taylor et al.
3,565,080 A 2/1971 Ide et al.
(Continued)

FOREIGN PATENT DOCUMENTS

EP 1575010 A1 9/2005
FR 2920087 A1 2/2009
(Continued)

OTHER PUBLICATIONS

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.
(Continued)

*Primary Examiner* — Devin Henson
(74) *Attorney, Agent, or Firm* — Quinn Law Group, PLLC

(57) ABSTRACT

A method of identifying a change in the health of a nerve during a surgical procedure includes determining a sensitivity of the nerve at a first time, determining a sensitivity of the nerve at a second time, and providing an indication to a user corresponding to a change in the sensitivity of the nerve from the first time to the second time. In each instance, the sensitivity of the nerve is determined by providing an electrical stimulus via an electrode disposed on a distal end portion of an elongate medical instrument, and monitoring a magnitude of a mechanical response of a muscle innervated by the nerve.

13 Claims, 10 Drawing Sheets

(56) References Cited

U.S. PATENT DOCUMENTS

| | | |
|---|---|---|
| 3,797,010 A | 3/1974 | Adler et al. |
| 4,817,628 A | 4/1989 | Zealear et al. |
| 5,284,153 A | 2/1994 | Raymond et al. |
| 5,284,154 A | 2/1994 | Raymond et al. |
| 5,775,331 A | 7/1998 | Raymond et al. |
| 6,324,432 B1 | 11/2001 | Rigaux et al. |
| 6,361,508 B1 | 3/2002 | Johnson et al. |
| 6,466,817 B1 | 10/2002 | Kaula et al. |
| 6,500,128 B2 | 12/2002 | Marino |
| 6,564,078 B1 | 5/2003 | Marino et al. |
| 6,760,616 B2 | 7/2004 | Hoey et al. |
| 6,807,438 B1 | 10/2004 | Brun Del Re et al. |
| 6,972,199 B2 | 12/2005 | Lebouitz et al. |
| 7,050,848 B2 | 5/2006 | Hoey et al. |
| 7,079,883 B2 | 7/2006 | Marino et al. |
| 7,177,677 B2 | 2/2007 | Kaula et al. |
| 7,207,949 B2 | 4/2007 | Miles et al. |
| 7,216,001 B2 | 5/2007 | Hacker et al. |
| 7,236,832 B2 | 6/2007 | Hemmerling et al. |
| 7,470,236 B1 | 12/2008 | Kelleher et al. |
| 7,522,953 B2 | 4/2009 | Kaula et al. |
| 7,578,819 B2 | 8/2009 | Bleich et al. |
| 7,582,058 B1 | 9/2009 | Miles et al. |
| 7,657,308 B2 | 2/2010 | Miles et al. |
| 7,664,544 B2 | 2/2010 | Miles et al. |
| 7,668,588 B2 | 2/2010 | Kovacs |
| 7,691,057 B2 | 4/2010 | Miles et al. |
| 7,892,173 B2 | 2/2011 | Miles et al. |
| 7,905,840 B2 | 3/2011 | Pimenta et al. |
| 7,942,826 B1 | 5/2011 | Scholl et al. |
| 7,959,577 B2 | 6/2011 | Schmitz et al. |
| 7,962,191 B2 | 6/2011 | Marino et al. |
| 7,981,058 B2 | 7/2011 | Akay |
| 7,991,463 B2 | 8/2011 | Kelleher et al. |
| 8,000,782 B2 | 8/2011 | Gharib et al. |
| 8,016,776 B2 | 9/2011 | Bourget et al. |
| 8,027,716 B2 | 9/2011 | Gharib et al. |
| 8,055,349 B2 | 11/2011 | Gharib et al. |
| 8,068,912 B2 | 11/2011 | Kaula et al. |
| 8,075,499 B2 | 12/2011 | Nathan et al. |
| 8,090,436 B2 | 1/2012 | Hoey et al. |
| 8,133,173 B2 | 3/2012 | Miles et al. |
| 8,137,284 B2 | 3/2012 | Miles et al. |
| 8,147,421 B2 | 4/2012 | Farquhar et al. |
| 8,165,653 B2 | 4/2012 | Marino et al. |
| 8,343,065 B2 | 1/2013 | Bartol et al. |
| 8,343,079 B2 | 1/2013 | Bartol et al. |
| 8,517,954 B2 | 8/2013 | Bartol et al. |
| 2001/0031916 A1 | 10/2001 | Bennett et al. |
| 2002/0038092 A1 | 3/2002 | Stanaland et al. |
| 2002/0165590 A1 | 11/2002 | Crowe et al. |
| 2003/0074037 A1 | 4/2003 | Moore et al. |
| 2004/0077969 A1 | 4/2004 | Onda et al. |
| 2004/0186535 A1 | 9/2004 | Knowlton |
| 2004/0230138 A1 | 11/2004 | Inoue et al. |
| 2004/0243018 A1 | 12/2004 | Organ et al. |
| 2005/0075578 A1 | 4/2005 | Gharib et al. |
| 2005/0085741 A1 | 4/2005 | Hoskonen et al. |
| 2005/0102007 A1 | 5/2005 | Ayal et al. |
| 2005/0240086 A1 | 10/2005 | Akay |
| 2005/0245839 A1 | 11/2005 | Stivoric et al. |
| 2005/0280531 A1 | 12/2005 | Fadem et al. |
| 2005/0283204 A1 | 12/2005 | Buhlmann et al. |
| 2006/0020177 A1 | 1/2006 | Seo et al. |
| 2006/0052726 A1 | 3/2006 | Weisz et al. |
| 2006/0135888 A1 | 6/2006 | Mimnagh-Kelleher et al. |
| 2006/0270949 A1 | 11/2006 | Mathie et al. |
| 2007/0038155 A1 | 2/2007 | Kelly, Jr. et al. |
| 2007/0265675 A1 | 11/2007 | Lund et al. |
| 2007/0276270 A1 | 11/2007 | Tran |
| 2008/0051643 A1 | 2/2008 | Park et al. |
| 2008/0058656 A1 | 3/2008 | Costello et al. |
| 2008/0167695 A1 | 7/2008 | Tehrani et al. |
| 2008/0234767 A1 | 9/2008 | Salmon et al. |
| 2008/0287761 A1 | 11/2008 | Hayter et al. |
| 2008/0306363 A1 | 12/2008 | Chaiken et al. |
| 2008/0306397 A1 | 12/2008 | Bonmassar et al. |
| 2008/0312560 A1 | 12/2008 | Jamsen et al. |
| 2008/0312709 A1 | 12/2008 | Volpe et al. |
| 2009/0036747 A1 | 2/2009 | Hayter et al. |
| 2009/0062696 A1 | 3/2009 | Nathan et al. |
| 2009/0069709 A1 | 3/2009 | Schmitz et al. |
| 2009/0069722 A1 | 3/2009 | Flaction et al. |
| 2009/0076336 A1 | 3/2009 | Mazar et al. |
| 2009/0171381 A1* | 7/2009 | Schmitz ............... A61B 5/0488 606/167 |
| 2009/0192416 A1 | 7/2009 | Ernst et al. |
| 2009/0228068 A1 | 9/2009 | Buhlmann et al. |
| 2009/0247910 A1 | 10/2009 | Klapper |
| 2009/0306741 A1 | 12/2009 | Hogle et al. |
| 2009/0318779 A1 | 12/2009 | Tran |
| 2010/0137748 A1 | 6/2010 | Sone et al. |
| 2010/0152619 A1 | 6/2010 | Kalpaxis et al. |
| 2010/0152622 A1 | 6/2010 | Teulings |
| 2010/0152623 A1 | 6/2010 | Williams |
| 2010/0168559 A1 | 7/2010 | Tegg et al. |
| 2010/0292617 A1 | 11/2010 | Lei et al. |
| 2011/0004207 A1 | 1/2011 | Wallace et al. |
| 2011/0237974 A1 | 9/2011 | Bartol et al. |
| 2012/0053491 A1 | 3/2012 | Nathan et al. |
| 2013/0123659 A1 | 5/2013 | Bartol et al. |
| 2013/0253533 A1 | 9/2013 | Bartol et al. |
| 2015/0032022 A1* | 1/2015 | Stone ................ A61B 5/04001 600/547 |

FOREIGN PATENT DOCUMENTS

| | | |
|---|---|---|
| WO | 0078209 A2 | 12/2000 |
| WO | 2007024147 A1 | 3/2007 |

OTHER PUBLICATIONS

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference BIOSIGNAL 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

\* cited by examiner

SYSTEM AND METHOD FOR ASSESSING NEURAL HEALTH

CROSS REFERENCE TO RELATED APPLICATIONS

This application is a continuation-in-part of and claims the benefit of priority from U.S. patent application Ser. No. 13/293,389, filed Nov. 10, 2011, which is hereby incorporated by reference in its entirety.

TECHNICAL FIELD

The present invention relates generally to a device to assess differences and/or changes in neural function through mechanical sensing.

BACKGROUND

During certain surgical procedures, tissue may need to be displaced to gain access to an otherwise inaccessible organ. For example, during a lateral approach to the lumbar spine, muscle tissue may need to be retracted to access one or more vertebrae or spinal discs. As this muscle tissue is displaced, embedded nerves may be stretched or strained in a manner that imposes gradual injury. Depending on the severity and duration, this injury may result in temporary loss of motor control or sensation in the muscle that nerve innervates.

SUMMARY

A method of identifying a change in the health of a nerve during a surgical procedure includes determining a sensitivity of the nerve via Mechanomyography at a first time, determining a sensitivity of the nerve via Mechanomyography at a second time, and providing an indication to a user corresponding to the difference in nerve sensitivity between the first time and the second time. The difference in sensitivity corresponds to the change in the health of a nerve.

Determining a sensitivity of the nerve may include providing an electrical stimulus via an electrode disposed on a distal end portion of an elongate medical instrument. The elongate medical instrument may be suitably configured to extend within the intracorporeal treatment area. Once the stimulus is provided, the method includes monitoring a magnitude of a mechanical response of the muscle that is artificially induced by the electrical stimulus. Such monitoring may include generating a mechanomyography output signal from a non-invasive mechanical sensor configured to be disposed in mechanical communication with the muscle of the subject, wherein the mechanomyography output signal corresponds to a mechanical movement of the muscle.

In another embodiment, determining a sensitivity of the nerve includes: determining the minimum electrical stimulus that must be provided to the nerve to artificially induce a mechanical response of the muscle.

A neural monitoring system for determining a change in the health of a nerve of a subject over a period of time may include a stimulator, a non-invasive mechanical sensor, and a processor. The stimulator is configured to extend within an intracorporeal treatment region of the subject and to provide an electrical stimulus therein. The non-invasive mechanical sensor is configured to be placed in communication with a muscle of the subject and to generate a mechanomyography output signal corresponding to a response of the muscle to the electrical stimulus.

The processor is in communication with the stimulator and with the sensor, and is configured to: provide a first electrical stimulus via the stimulator at a first time; and determine a first amplitude of the mechanomyography output signal that corresponds to a response of the muscle to the first electrical stimulus. Subsequently, the processor may provide a second electrical stimulus via the stimulator at a second time; and determine a second amplitude of the mechanomyography output signal that corresponds to a response of the muscle to the second electrical stimulus. Once the first and second electrical stimuli are provided, the processor may provide an indication to a user, via a display, that corresponds to a difference between the first amplitude and the second amplitude. The difference may be indicative of a change in the health of the nerve.

The above features and advantages and other features and advantages of the present invention are readily apparent from the following detailed description of the best modes for carrying out the invention when taken in connection with the accompanying drawings.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

Figure 1:
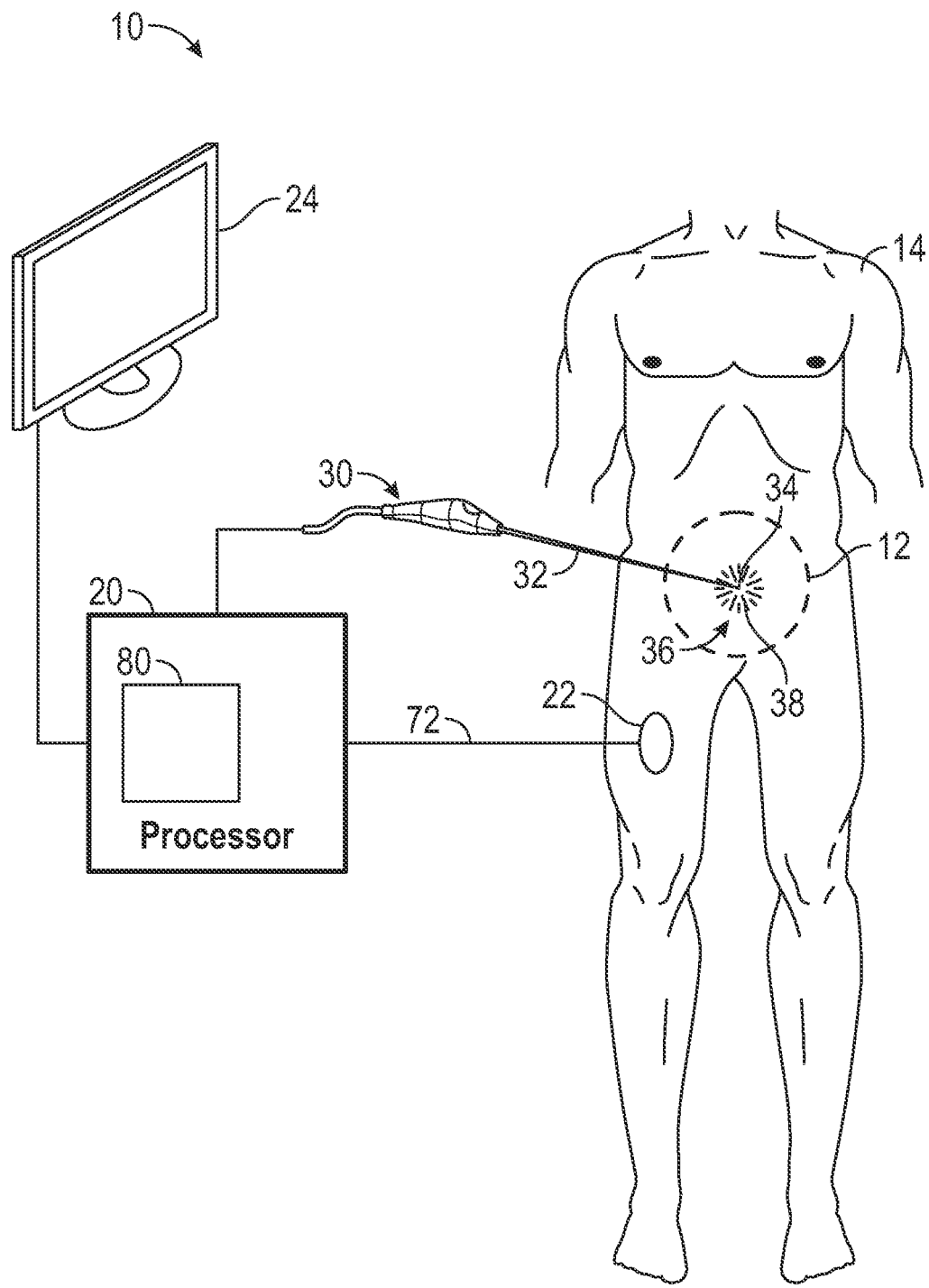
FIG. 1 is a schematic diagram of a neural monitoring system for detecting an artificially-induced mechanical muscle response.

Referring to the drawings, wherein like reference numerals are used to identify like or identical components in the various views, FIG. 1 schematically illustrates a neural monitoring system 10 that may be used to identify the presence of one or more nerves within an intracorporeal treatment area 12 of a subject 14. As will be described in greater detail below, the system 10 may monitor one or more muscles of the subject 14 for a mechanical motion, and may be capable of discriminating an artificially-induced mechanical response of a muscle (also referred to as an "artificially-induced mechanical muscle response") from a subject-intended muscle contraction/relaxation and/or an environmentally caused movement. If an artificially-induced mechanical muscle response is detected during the procedure, the system 10 may provide an indication to a user, such as via a display or perform another appropriate action.

As used herein, an artificially-induced mechanical muscle response refers to a contraction or relaxation of a muscle in response to a stimulus that is not received through natural sensory means (e.g., sight, sound, taste, smell, and touch). Instead, it is a contraction/relaxation of a muscle that is induced by the application of a stimulus directly to a nerve that innervates the muscle. Examples of stimuli that may cause an "artificially-induced" muscle response may include an electrical current applied directly to the nerve or to intracorporeal tissue or fluid immediately surrounding the nerve. In this example, if the applied electrical current is sufficiently strong and/or sufficiently close to the nerve, it may artificially cause the nerve to depolarize (resulting in a corresponding contraction of the muscle innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially-induced mechanical muscle response, a muscle innervated by the artificially depolarized nerve may physically contract or relax (i.e., a mechanical response). Such a mechanical reaction may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state, and is distinguished from other global translations of the muscle.

The neural monitoring system 10 may include a processor 20 that is in communication with at least one mechanical sensor 22 and a display 24. The mechanical sensor 22 may include, for example, a strain gauge, a force transducer, a position encoder, an accelerometer, a piezoelectric material, or any other transducer or combination of transducers that may convert a physical motion into a variable electrical signal.

Each mechanical sensor 22 may specially be configured to monitor a local mechanical movement of a muscle of the subject 14. For example, each sensor 22 may include a fastening means, such as an adhesive material/patch, that allows the sensor 22 to be adhered, bandaged, or otherwise affixed to the skin of the subject 14 (i.e. affixed on an external skin surface). Other examples of suitable fastening means may include bandages, sleeves, or other elastic fastening devices that may hold the sensor 22 in physical contact with the subject 14. Alternatively, the mechanical sensor 22 (and/or coupled device) may be configured to monitor a local mechanical movement of a muscle by virtue of its physical design. For example, the sensors/coupled devices may include catheters, balloons, bite guards, orifice plugs or endotracheal tubes that may be positioned within a lumen or natural opening of the subject to monitor a response of the lumen or orifice, or of a muscle that is directly adjacent to and/or connected with the lumen or orifice. In one configuration, the mechanical sensor may be a non-invasive device, whereby the term "non-invasive" is intended to mean that the sensor is not surgically placed within the body of the subject (i.e., via cutting of tissue to effectuate the placement). For the purposes of this disclosure, non-invasive sensors may include sensors that are placed within naturally occurring body lumens that are accessible without the need for an incision.

In one configuration, the sensor 22 may include a contact detection device, that may provide an indication if the sensor 22 is in physical contact with the skin of the subject 14. The contact detection device may, for example, include a pair of electrodes that are configured to contact the skin of the subject 14 when the sensor 22 is properly positioned. The sensor 22/contact detection device may then monitor an impedance between the electrodes to determine whether the electrodes are in contact with the skin. Other examples of suitable contact detection devices may include capacitive touch sensors or buttons that protrude slightly beyond the surface of the sensor.

The system 10 may further include one or more elongate medical instruments 30 that are capable of selectively providing a stimulus within the intracorporeal treatment area 12 of the subject 14 (i.e., also referred to as a stimulator 30). For example, in one configuration, the elongate medical instrument 30 may include a probe 32 (e.g., a ball-tip probe, k-wire, or needle) that has one or more electrodes 34 disposed on a distal end portion 36. The electrode(s) 34 may be selectively electrified, at either the request of a user/physician, or at the command of the processor 20, to provide an electrical stimulus 38 to intracorporeal tissue of the subject. In other configurations, the elongate medical instrument 30 may include a dialator, retractor, clip, cautery probe, pedicle screw, or any other medical instrument that may be used in an invasive medical procedure. Regardless of the instrument, if the intended artificial stimulus is an electrical current, the instrument 30 may include one or more selectively electrifiable electrodes 34 disposed at a portion of the instrument that is intended to contact tissue within the intracorporeal treatment area 12 during a procedure.

During a surgical procedure, in one configuration, the user/surgeon may selectively administer the stimulus to intracorporeal tissue within the treatment area 12 to identify the presence of one or more nerve bundles or fibers. For an electrical stimulus 38, the user/surgeon may administer the stimulus, for example, upon depressing a button or foot pedal that is in communication with the system 10, and more specifically in communication with the stimulator 30. In another configuration, the processor 20 may be configured to automatically provide the stimulus 38, for example, at a periodic interval, or when it senses a drop in impedance at the electrode 34 (i.e., indicating contact with tissue). The electrical stimulus 38 may, for example, be a discrete pulse (e.g., a step pulse) having a pulse width within the range of about 30 μs to about 500 μs. In other examples, the discrete pulse may have a pulse width within the range of about 50 μs to about 200 μs, or within the range of about 75 μs to about 125 μs. The discrete pulse may be periodically applied at a frequency of, for example, between about 1 Hz and about 10 Hz.

Figure 2:
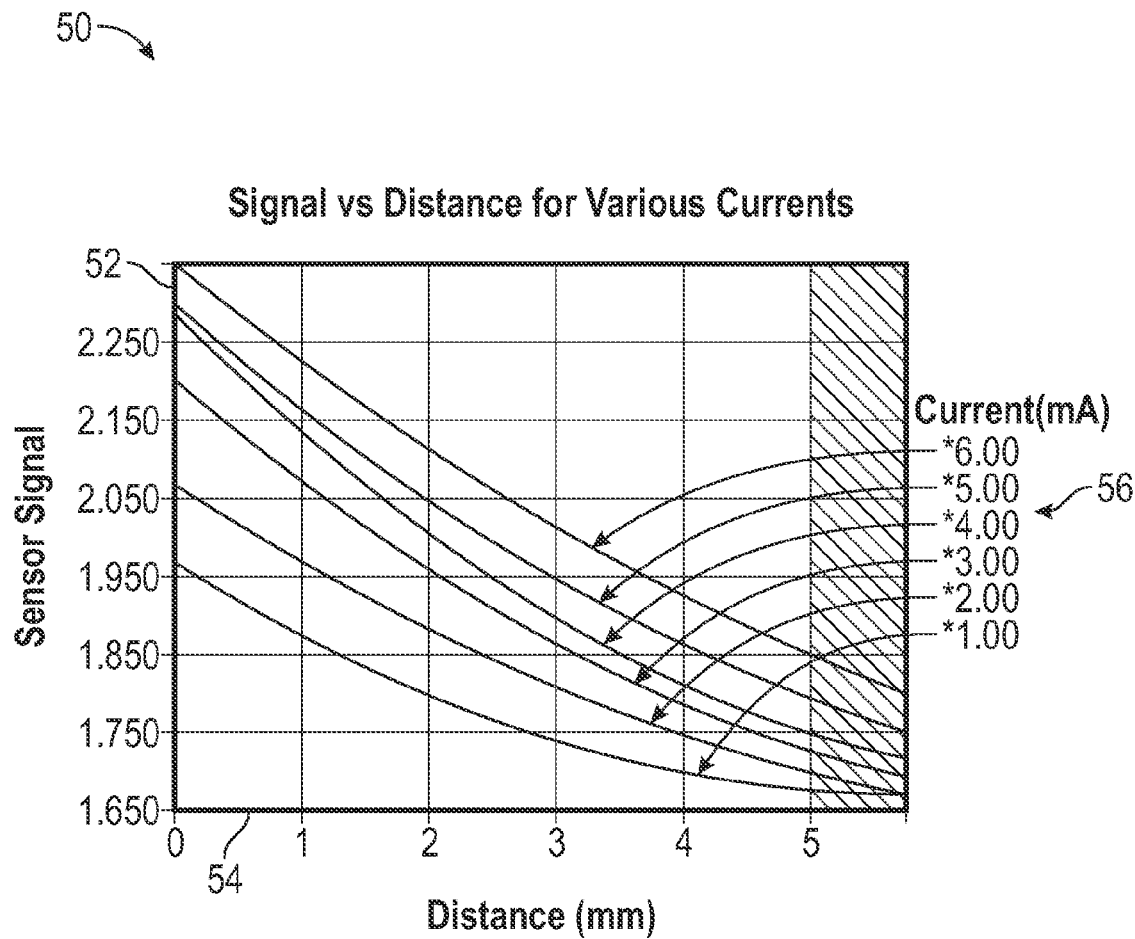
FIG. 2 is a schematic graph of the relationship between MMG output signal amplitude, stimulator electrical current, and distance between a stimulator electrode and a nerve.

If a nerve extends within a predetermined distance of the electrode 34, the electrical stimulus 38 may cause the nerve to depolarize, resulting in a mechanical twitch of a muscle that is innervated by the nerve (i.e., an artificially-induced mechanical muscle response). In general, the magnitude of the response/twitch may be directly correlated to the distance between the electrode and the nerve, and the magnitude of the stimulus current. FIG. 2 illustrates a graph 50 of these relationships, for a healthy nerve, where the magnitude 52 of the sensed response is shown as a function of the distance 54 between the stimulator and the nerve, and the magnitude 56 of the applied electrical current stimulus. In one configuration, the relationships illustrated in FIG. 2 (or variants thereof) may be stored in a lookup table associated with the processor 20. The lookup table may then be employed by the processor 20 to provide an approximate distance 54 between the electrode 34 and the nerve, given a known stimulus magnitude 56 and a measured mechanical muscle response magnitude 52.

Referring again to FIG. 1, prior to beginning a surgical procedure, the one or more mechanical sensors 22 may be placed in mechanical communication with one or more muscles of the subject 14. In the present context, a sensor 22 may be in mechanical communication with the muscle if it can physically detect a movement, velocity, acceleration, strain or other physical response of the muscle, either via direct contact with the muscle, or via a mechanical relationship through one or more intermediate materials and/or tissues (e.g., skin and/or subcutaneous tissue).

Figure 3:
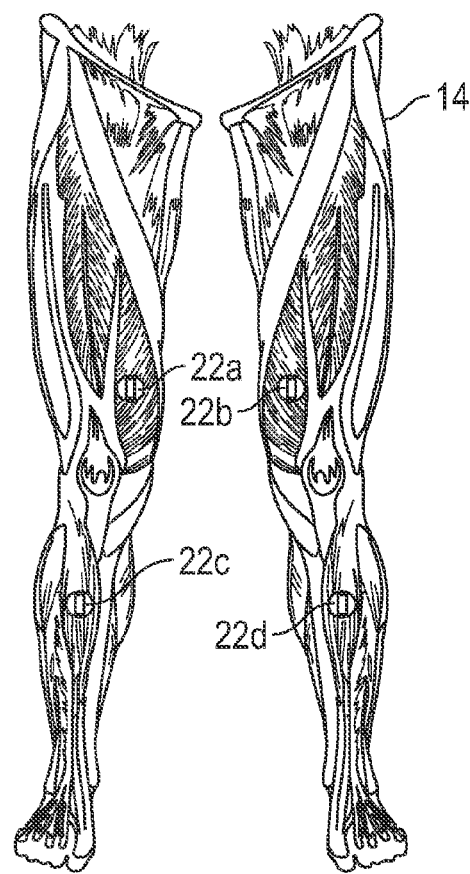
FIG. 3 is a schematic front view of the placement of a plurality of mechanical sensors on the legs of a subject.
Figure 4:
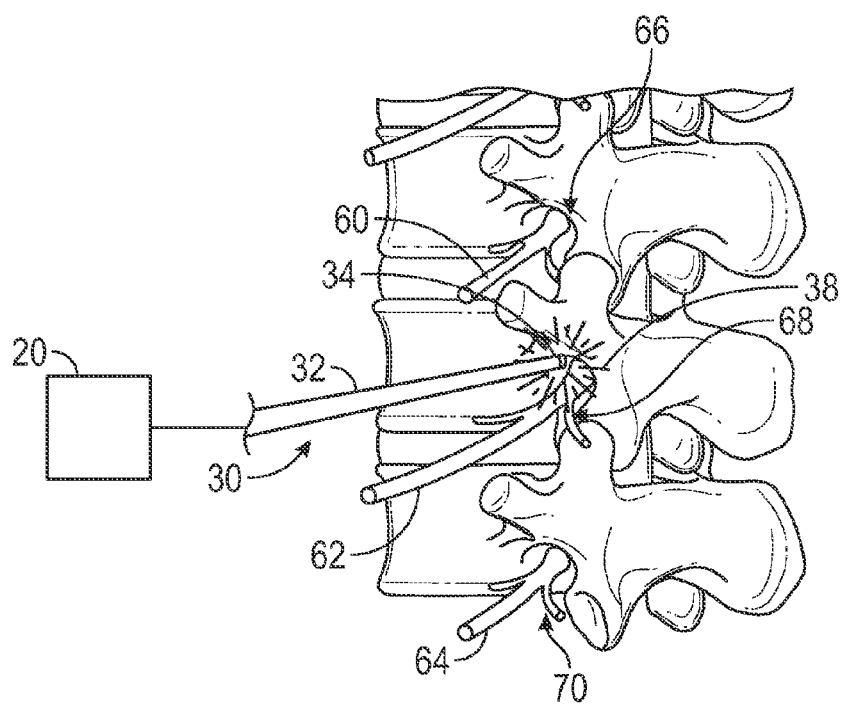
FIG. 4 is a schematic side view of an intracorporeal treatment area including a portion of the lumbar spine.

FIG. 3 illustrates an example of the placement of a plurality of mechanical sensors 22 for a surgical procedure that may occur proximate the L2, L3, and/or L4 vertebrae of the lumbar spine (shown schematically in FIG. 4). The nerves 60, 62 and 64 exiting the L2, L3 and L4 foramen 66, 68, 70 may therefore either lie within the treatment area 12 (i.e., the area surrounding the L2, L3, and/or L4 vertebrae), or may be immediately proximate to this area. Using common anatomical knowledge, the surgeon may understand that damage to these nerves 60, 62, 64 may affect the functioning of the vastus medialis muscles and the tibialis anterior muscles. As such, the surgeon may place mechanical sensors 22a-22d on or near the vastus medialis muscles and the tibialis anterior muscles to guard against inadvertent manipulation of the nerves during the procedure. For example, mechanical sensors 22a and 22b are placed on the vastus medialis muscles, which are innervated by the nerves 60, 62 exiting the L2 and L3 foramen 66, 68, and sensors 22c and 22d are placed on the tibialis anterior muscles, which are innervated by the nerves 64 exiting the L4 foramen 70.

In general, each mechanical sensor 22 may generate a mechanomyography (MMG) output signal (schematically shown in FIG. 1 at 72) that corresponds to a sensed mechanical movement/response of the adjacent muscle. The MMG output signal 72 may be either a digital or analog signal, and may typically be provided to the processor 20 through either wired or wireless communication means (e.g., through a physical wire, or using radio frequency communication protocols, such as according to IEEE 802.11 or another protocol such as Bluetooth). As a specific signal, the MMG output signal 72 is intended to be separate and distinct from any electrical potentials of the muscle or skin (often referred to as electromyography (EMG) signals). While electrical (EMG) and mechanical (MMG) muscle responses may be related, their relationship is complex, and not easily described (e.g., electrical potentials are very location specific, with a potentially variable electrical potential across the volume of the muscle of interest).

Referring again to FIG. 1, the processor 20 may be in communication with the stimulator 30 and the mechanical sensor 22, and may be configured to receive the MMG output signal 72 from the mechanical sensor 22. The processor 20 may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics.

The processor 20 may be configured to automatically perform one or more signal processing algorithms 80 or methods to determine whether a sensed mechanical movement (i.e., via the MMG output signal 72) is representative of an artificially-induced mechanical muscle response or if it is merely a subject-intended muscle movement and/or an environmentally caused movement. For example, the processor 20 may compute a time derivative of acceleration (da/dt) from the MMG output signal 72, and compare this computed value to a threshold to determine whether a detected muscle response was artificially-induced. Alternatively, the processor may use one or more digital detection techniques to determine if a mechanical response was artificially induced. Examples of such digital techniques are described in U.S. patent application Ser. No. 13/965,457 to Wybo et al., entitled "Neural Event Detection," which is hereby incorporated by reference in its entirety. These processing algorithms 80 may be embodied as software or firmware, and may either be stored locally on the processor 20, or may be readily assessable by the processor 20.

In one configuration, the neural monitoring system 10 may be used to assess the function and/or health of a nerve before, during, and/or after a surgical procedure. In general, damage to a nerve tends to attenuate neurologic signals that may be transmitted to a muscle via the nerve. Healthy nerves tend to elicit greater muscle responses than damaged nerves for a given stimulus, and artificially-induced muscle responses may be detected at lower stimulus magnitudes with healthy nerves than with damaged nerves. Therefore, in one configuration, the neural monitoring system 10 may be configured to assess the health of a nerve by monitoring the magnitude of a muscle response to a fixed-current electrical stimulus. In another configuration the neural monitoring system 10 may be configured to assess the health of a nerve by determining the minimum current required to artificially induce a mechanical muscle response.

These nerve-health monitoring techniques may be used, for example, to determine an absolute health of a nerve, such as by comparing a measured response against a control (e.g., where the control may be established by testing a known, healthy nerve). In another configuration, these techniques may also be used to quantify changes in nerve function that may occur during a procedure, or changes in nerve function that may be attributable to the procedure.

Figure 5:
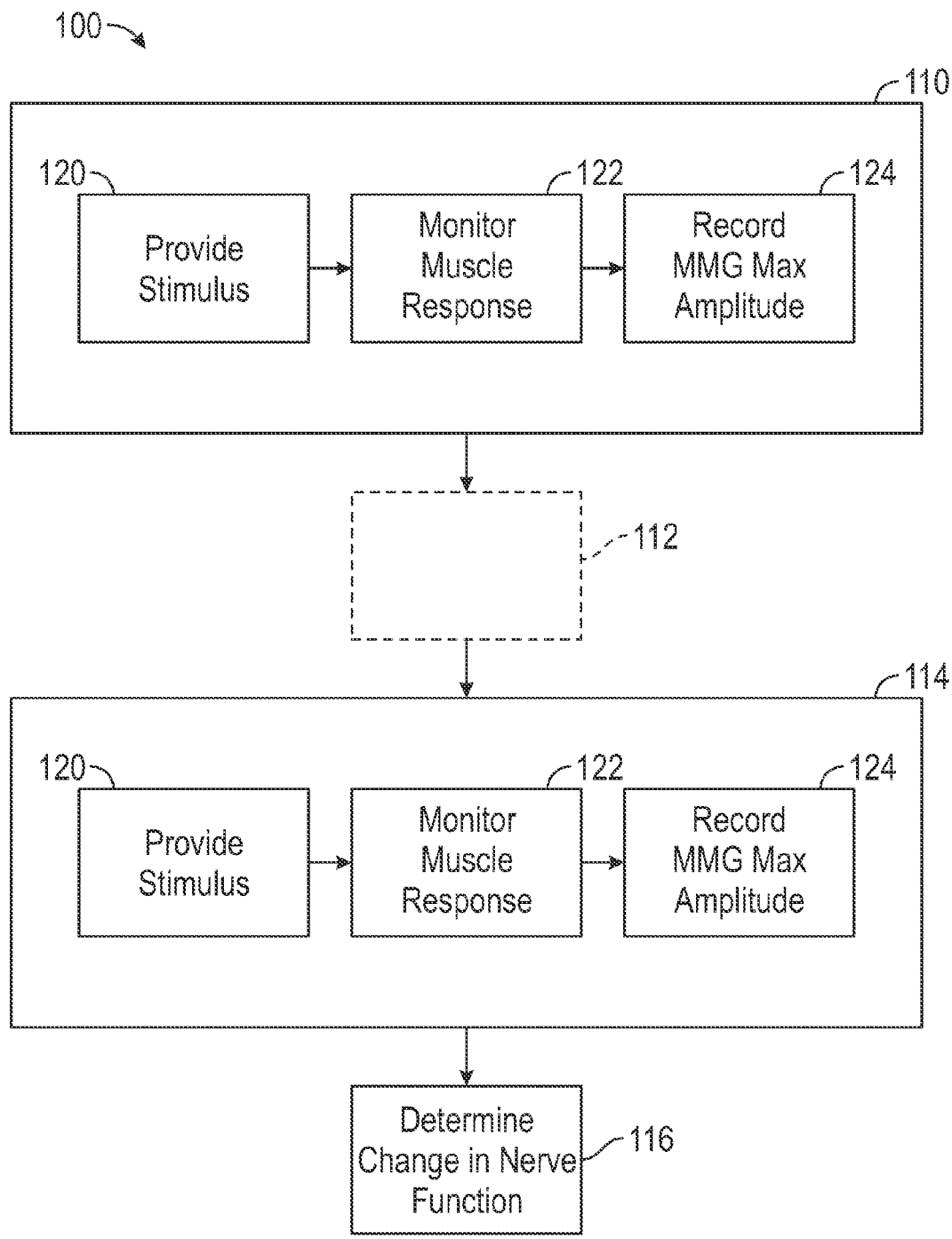
FIG. 5 is schematic flow diagram illustrating a method of identifying a change in nerve health.
Figure 6:
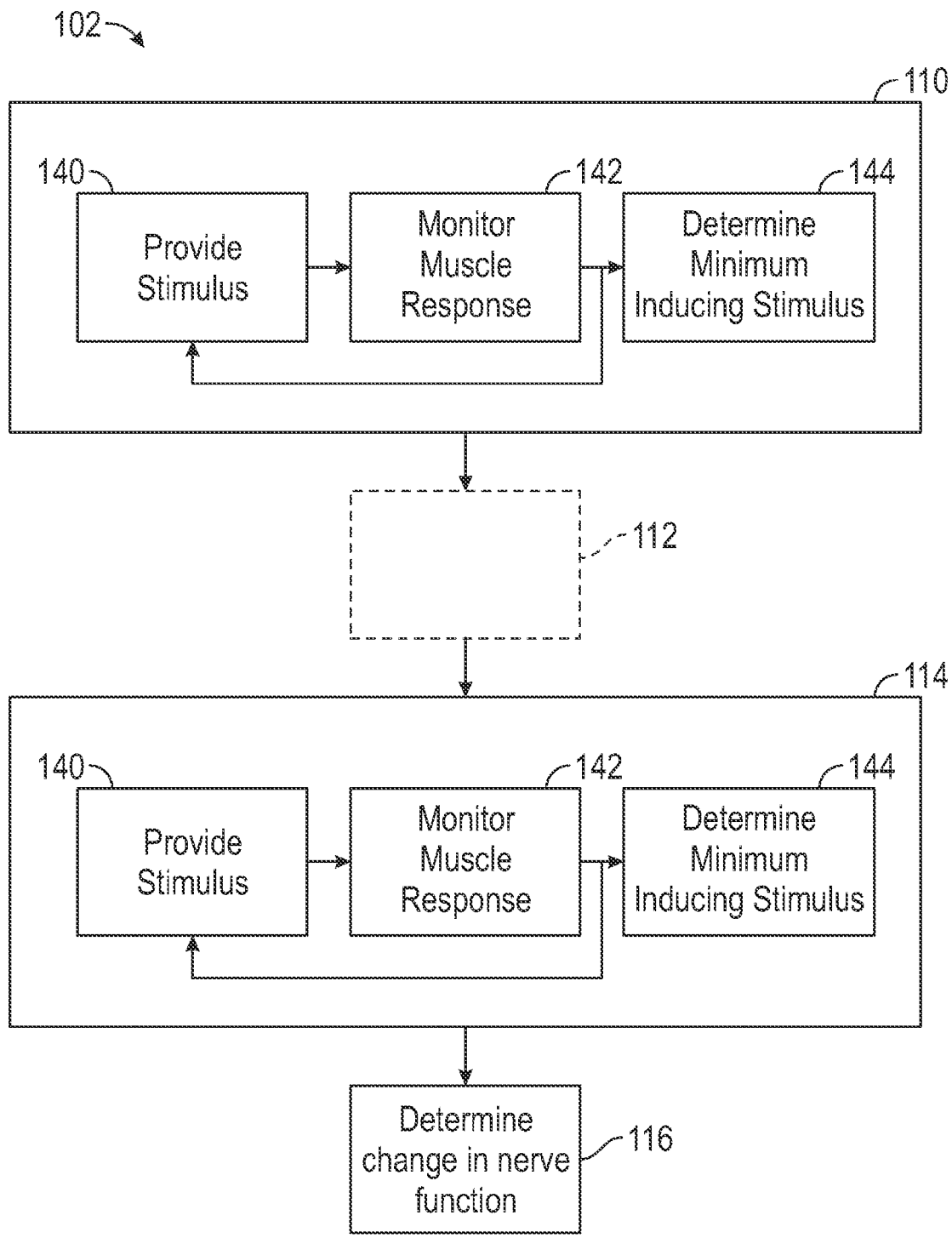
FIG. 6 is schematic flow diagram illustrating a method of identifying a change in nerve health.

FIGS. 5 and 6 schematically illustrate how the above-described techniques may be used to assess a change in nerve function. As shown each method 100, 102 begins by establishing a baseline nerve function value at a first time ($T_1$) (step 110). After a period of time (schematically illustrated at 112), the system 10 is then used to establish a subsequent nerve function value at a second time ($T_2$) (step 114); and finally, the processor 20 may then compare the subsequent nerve function value with the baseline nerve function value in step 116 to determine a change in nerve function. This determined change may provide a quantitative indication of a change in nerve health to a user, and may be graphically or textually displayed via the display 24.

Referring specifically to FIG. 5, in each of the steps where a nerve function value is established, the processor 20 may begin at step 120 by providing an electrical stimulus 38 to an electrode 34 at a fixed current level ($I_1$). At step 122, the processor 20 may then monitor the MMG output signal 72 for an artificially-induced mechanical muscle response that corresponds to the provided stimulus 38. Finally in step 124, the processor 20 may record the maximum MMG amplitude that corresponds to the detected muscle response.

Figure 7:
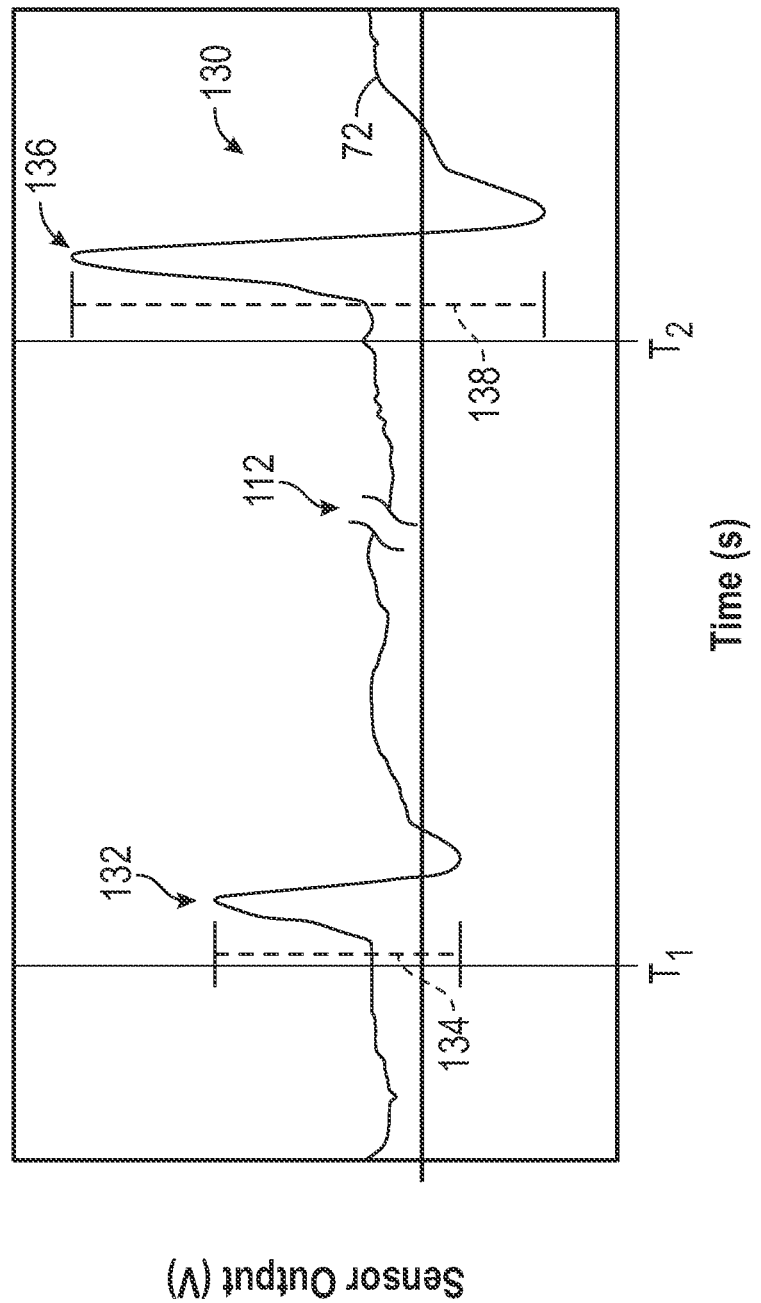
FIG. 7 is a graph of a mechanomyography signal, such as from an accelerometer in mechanical communication with a muscle of a subject, illustrating a first and a second muscle response.

The method 100 may be illustrated, for example, by the graph 130 provided in FIG. 7, which may schematically represent an MMG output signal 72 at the two testing times $T_1$ and $T_2$. As shown, at time $T_1$ a first mechanical muscle response 132 is artificially induced and detected, and may have first magnitude 134. At the second time $T_2$, a second mechanical muscle response 136 is artificially induced and detected, and may have a second magnitude 138. The processor 20 may automatically compare the second magnitude 138 with the first magnitude 134 to determine that the health of the corresponding nerve has improved in the time between $T_1$ and $T_2$. The quantitative difference (either in absolute terms, or in a percent difference) may then be provided to a user via a display 24 or a report. During the interim time between $T_1$ and $T_2$, a surgeon may have, for example, performed a procedure (e.g., a nerve root decompression) that relieved an applied pressure from the nerve.

Referring to FIG. 6, instead of monitoring for a variable muscle response, the processor 20 may determine a variable minimum current needed to artificially induce a muscle response. As shown, the processor 20 may begin at step 140 by providing an electrical stimulus 38 to an electrode 34 at a variable current level ($I_v$). In one configuration, the variable current may be in the range of from about 0.1 mA to about 20 mA. At step 142, the processor 20 may then monitor the MMG output signal 72 for an artificially-induced mechanical muscle response that corresponds to the provided stimulus. In a closed loop manner, the processor 20 may determine the minimum current level that may induce a muscle response, which may then be recorded in step 144. Using this method 102, the processor 20 may compare the recorded minimum stimulus at a first time ($T_1$) with the recorded minimum stimulus at a second time ($T_2$) to determine a change in nerve function or health.

In one configuration, the above described methods 100, 102 may be useful, for example, in determining the efficacy of a nerve root decompression procedure, such as a foraminotomy, laminectomy, or discectomy that may remove an impingement from a nerve. The impingement may include, for example, a bone spur, herniated disc, or inflamed tissue, which may be surgically removed to alleviate pressure against a nerve. These procedures may improve the functioning of the nerve, though the amount and nature of the improvement are highly dependent on the duration and degree of the compression. To quantify the improvement, either of the above described methods 100, 102 may be used to first establish a baseline functioning (step 110) at a first time $T_1$ (i.e., a time prior to the decompression procedure), and to then retest the nerve functioning (step 114) at a second time $T_2$ (i.e., a time after the decompression procedure). By comparing the post procedure response with the pre-procedure response, the system 10 may indicate to the surgeon whether additional treatment may be required.

Figure 8:
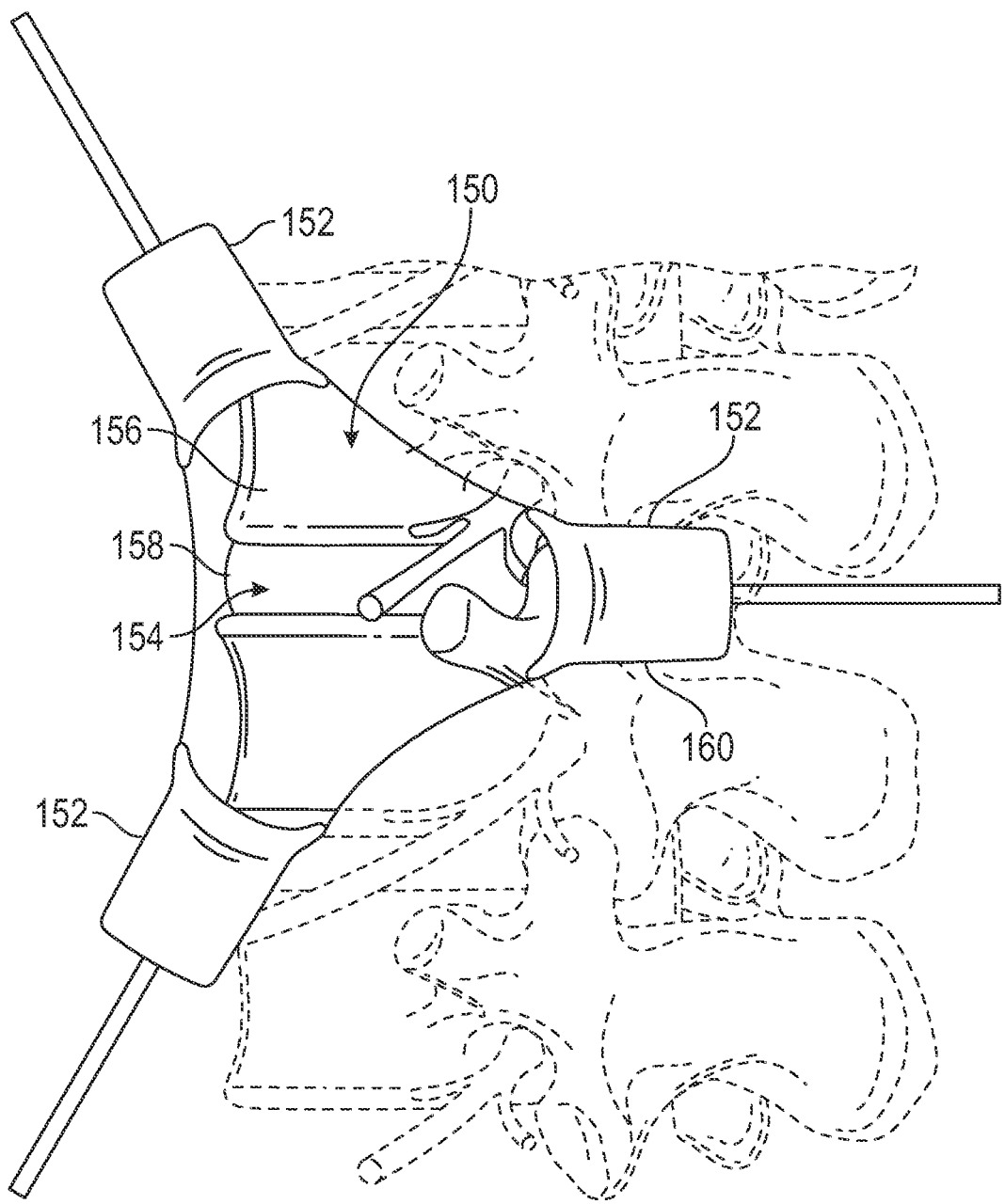
FIG. 8 is a schematic top view of a plurality of retractor blades forming an intraoperative corridor to access an intracorporeal treatment area of a subject.
Figure 9:
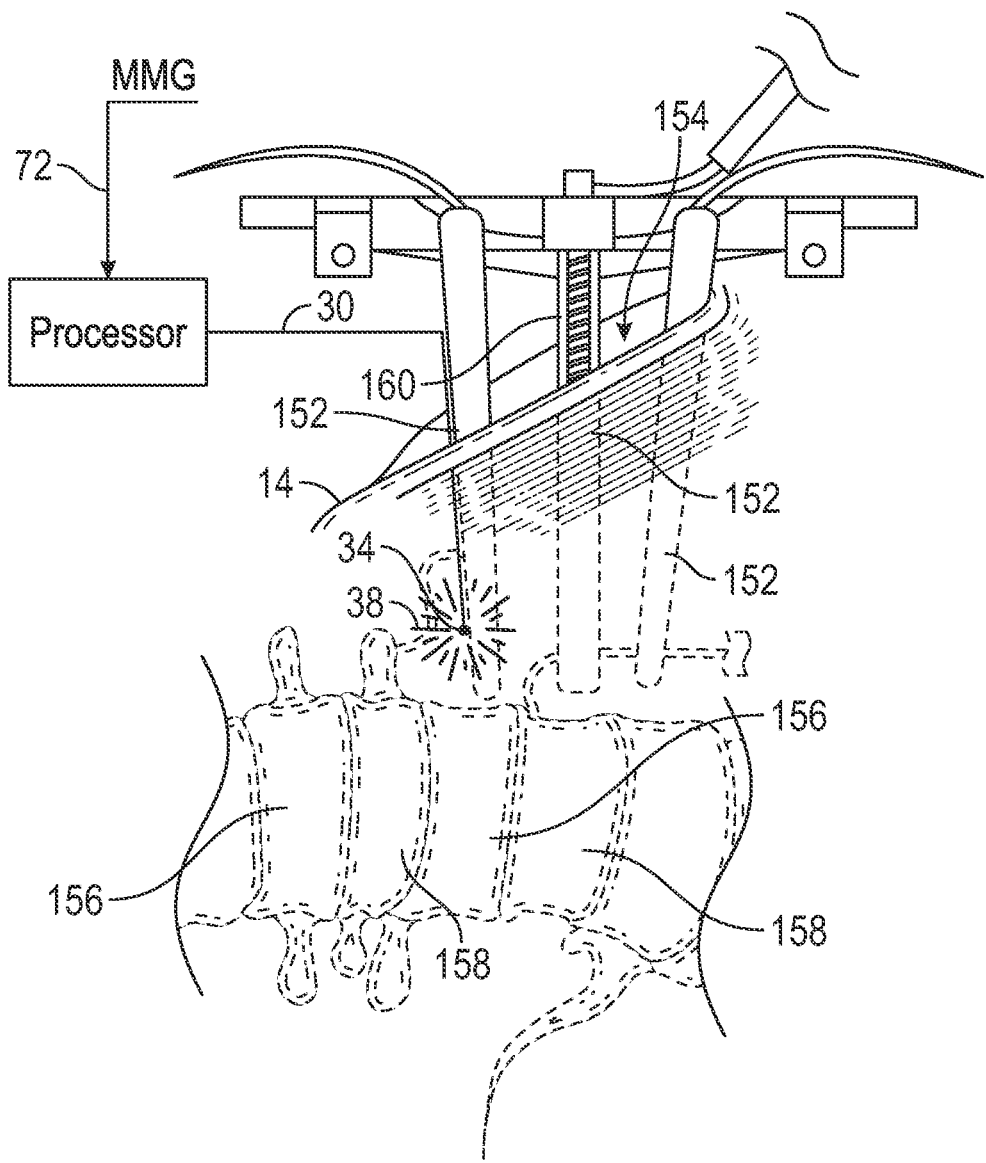
FIG. 9 is a schematic side view of a plurality of retractor blades forming an intraoperative corridor to access an intracorporeal treatment area of a subject.

While the above example involves assessing nerve function prior to a decompression procedure, and reassessing the nerve function after the decompression procedure, in another configuration the system 10 may similarly be used to evaluate nerve function or health throughout the duration of a procedure. For example, FIGS. 7 and 8 illustrate a lateral approach to a spine 150 where a plurality of retractor blades 152 are used to separate and restrain tissue (particularly the psoas muscle) to provide an intraoperative corridor 154. A surgeon may use the intraoperative corridor 154 to access a vertebrae 156 or disk 158 to perform a therapeutic procedure.

During tissue retraction, one or more nerves may be displaced, stretched, or strained by the movement and separation of the psoas muscle fibers by the retractor blades 152. It has been found that such stretching/straining of the nerves may result in a partial or total loss of sensory perception and/or motor control for at least a temporary period of time. For some procedures, the length of time that nerve function is compromised following the procedure may be a function of the amount of strain imposed to a nerve, together with the length of time the strain is imposed for.

In a similar manner as testing nerve function/health before and after a complete procedure, the above-described methods 100, 102 may also be used to monitor changes in nerve health throughout the procedure. In this manner, the surgeon may be provided with a periodic assessment of the health (or change in health) of the nerves that are proximate to the intraoperative corridor 154.

To accomplish the periodic monitoring, as generally illustrated in FIG. 8, in one configuration one or more of the plurality of retractor blades 152 may include an electrode 34 that is configured to provide an electrical stimulus 38 to the surrounding intracorporeal tissue. In one configuration, the electrode 34 may be disposed on a side of the blade 152 that is opposite the intraoperative corridor 154. Likewise, the electrode 34 may be configured so that it makes leading contact with the surrounding tissue. While the electrode 38 is schematically illustrated immediately adjacent to the retractor blade 152, in different configurations, it may be either integrated with the retractor blade 152, it may be carried by the retractor blade 152 (such as with a holstered probe), or it may be merely adjacent to the retractor blade 152, such as by inserting a needle electrode/probe into the tissue. While each retractor blade 152 may be configured to provide an electrical stimulus 34, in certain procedures, such as a lateral spinal approach, it may be particularly beneficial to configure at least a posterior blade 160 as a stimulator 30 (or to dispose a stimulator in a fixed position adjacent to the posterior retractor blade 160).

Figure 10:
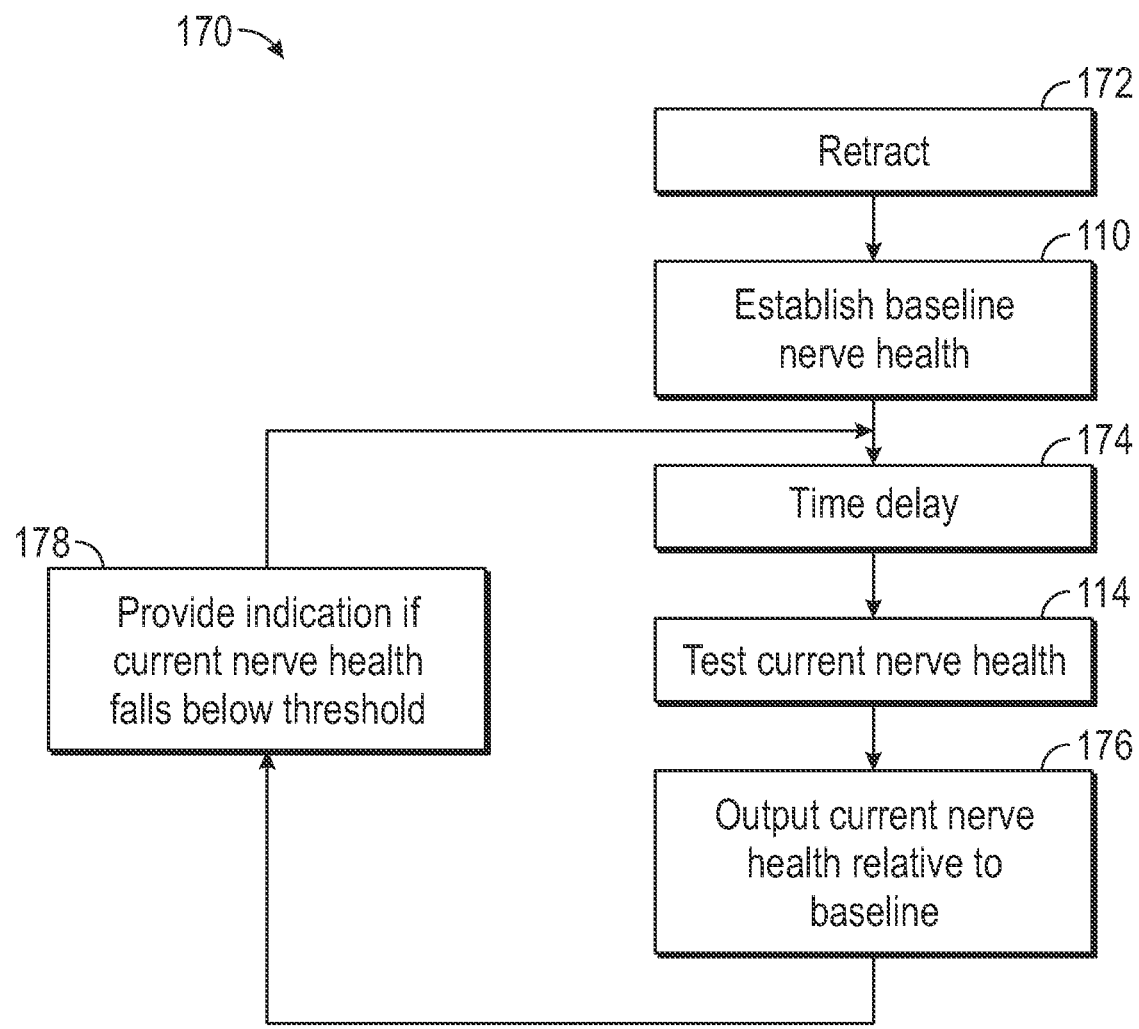
FIG. 10 is a schematic flow diagram illustrating a method of monitoring the health of a nerve throughout the duration of a procedure.

FIG. 10 schematically illustrates a method 170 of monitoring the health of a nerve throughout the duration of a procedure. The method 170 may begin, for example, at step 172 when tissue is retracted to form an intraoperative corridor 154. Immediately following retraction, presumably when the retractor blades have been locked in place, the system 10 may establish a baseline level of nerve functioning/health 110, such as by providing an electrical stimulus 34 via an electrode integrated with, or disposed adjacent to a retractor blade 152. After a predefined time delay at 174, the system 10 may retest the nerve functioning/health 114 in a similar manner as it used to establish a baseline at 110. The predefined time delay, may be, for example, in the range of about 5 seconds to about 300 seconds, or in other embodiments, may be less than 5 seconds.

Once the system 10 retests the nerve functioning/health at 114, it may then output the retested level (from step 114) relative to the baseline (from step 110) to a user at step 176. In one configuration, the output may be provided as a rolling graph, a bar graph, a numerical value or some other form of similar visual graphic that may be provided via the display 24. Finally, in step 178, the system 10 may compare the retested value to a threshold, and may provide an indication to a user if the nerve health falls below the threshold.

Figure 11:
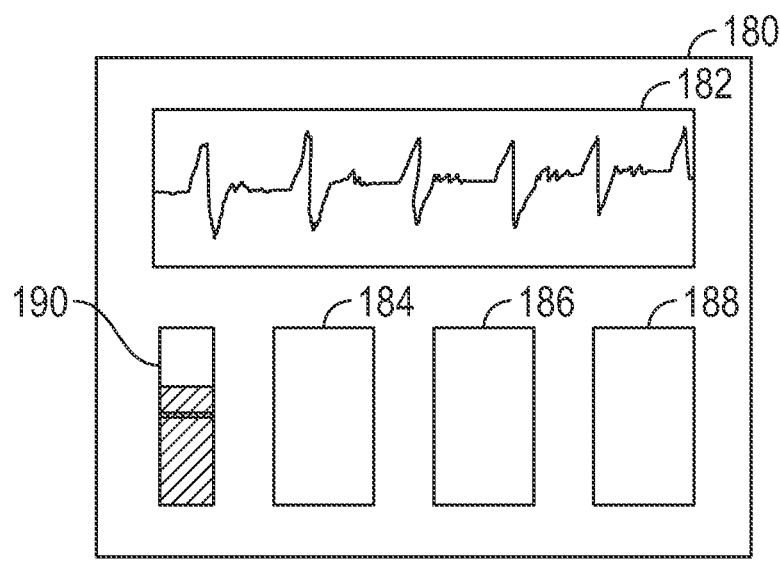
FIG. 11 is a schematic view of an integrated display used to display a plurality of patient vitals.
Figure 12:
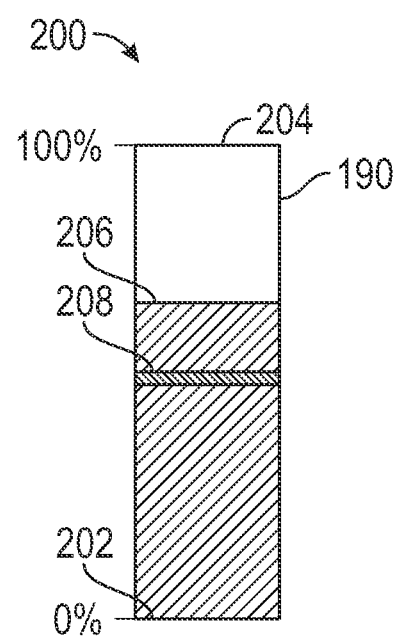
FIG. 12 is a schematic enlarged view of a nerve health monitoring graphic, such as included in the display of FIG. 11.

FIG. 11 schematically illustrates one embodiment of an integrated display 180 that may be similar to the display 24 mentioned with respect to FIG. 1. In this configuration, the display 180 may include various patient vitals, such as, for example, heart rhythm (electrocardiogram) 182, pulse 184, blood pressure 186, pulse oximetry 188, and nerve health 190. FIG. 12 provides an enlarged view of a nerve health monitoring graphic 200 that may be provided to a surgeon. As shown, the graphic 200 may be a bar chart that normalizes nerve functioning between no functioning 202 and the baseline level 204 (from step 110). In the embodiment shown, the height of the bar graph 206 may represent the current/retested nerve health (from step 114) as a percent of the baseline. The bar graph may then be continuously updated at the periodic interval as the nerve function is retested. The graphic 200 may further illustrate a threshold level 208 that may be set prior to surgery by the physician. If the height of the bar graph 206 falls below the threshold level 208, the system 10 may provide an indication to the user that, for example, temporary nerve damage may occur if the strain is maintained through the nerve. This may queue the surgeon to conclude the procedure (in advance of reaching the threshold), and/or may serve as an indication to temporarily relax the retractor.

While the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

The invention claimed is:

1. A method of identifying a change in the health of a nerve during a surgical procedure, wherein the nerve extends within an intracorporeal treatment area of a subject and innervates a muscle of the subject, the method comprising:
determining a sensitivity of the nerve via Mechanomyography periodically throughout the surgical procedure;
providing an indication to a user corresponding to a difference in nerve sensitivity between a first time during the procedure and a second time during the procedure; and
wherein the difference in nerve sensitivity corresponds to the change in the health of a nerve; and
wherein determining the sensitivity of the nerve includes:
providing an electrical stimulus via an electrode disposed on a distal end portion of an elongate medical instrument, the elongate medical instrument being configured to extend within the intracorporeal treatment area; and
receiving a mechanomyography output signal generated by a non-invasive mechanical sensor disposed in mechanical communication with the muscle of the subject, the mechanomyography output signal corresponding to a mechanical movement of the muscle that is induced by the electrical stimulus.

2. The method of claim 1, wherein determining a sensitivity of the nerve further includes:
determining the minimum electrical stimulus that must be provided to the nerve to artificially induce a mechanical response of the muscle; and
wherein the minimum electrical stimulus is indicative of the sensitivity of the nerve.

3. The method of claim 1, wherein determining a sensitivity of the nerve at both the first time and at the second time further includes:
determining a peak amplitude of the mechanomyography output signal; and
wherein the peak amplitude is indicative of the sensitivity of the nerve.

4. A method of identifying a change in the health of a nerve during a surgical procedure, wherein the nerve extends within an intracorporeal treatment area of a subject and innervates a muscle of the subject, the method comprising:
determining a sensitivity of the nerve periodically throughout the surgical procedure by:
providing an electrical stimulus via an electrode disposed on a distal end portion of an elongate medical instrument configured to extend within the intracorporeal treatment area;
monitoring a magnitude of a mechanical response of the muscle, wherein the mechanical response of the muscle is artificially induced by the electrical stimulus;
providing an indication to a user corresponding to a difference between the magnitude of the mechanical response at a first time during the surgical procedure and the magnitude of the mechanical response at a second time during the surgical procedure, and wherein the difference is indicative of a change in the health of the nerve; and
wherein monitoring the magnitude of the mechanical response includes receiving a mechanomyography output signal generated by a non-invasive mechanical sensor disposed in mechanical communication with the muscle, the mechanomyography output signal corresponding to a mechanical movement of the muscle that is induced by the electrical stimulus.

5. The method of claim 4, wherein providing an indication to a user includes displaying, via a display device, the magnitude of the second mechanical response as a percentage of the magnitude of the first mechanical response.

6. The method of claim 5, further comprising providing an indication to a user corresponding to the difference between the magnitude of the second mechanical response and a predefined threshold.

7. The method of claim 4, further comprising, retracting tissue within the intracorporeal treatment area of a subject between the first time and the second time.

8. The method of claim 7, wherein the tissue includes a portion of a psoas muscle of the subject.

9. The method of claim 7, wherein the elongate medical instrument is a retractor blade used to retract the tissue within the intracorporeal treatment area of a subject.

10. The method of claim 4, wherein the electrical stimulus is provided at a common current at both the first time and the second time.

11. The method of claim 4, wherein providing the electrical stimulus via the electrode includes transmitting an electrical current from the electrode to tissue of the subject within the intracorporeal treatment region.

12. The method of claim 4, wherein the first time and the second time are from about 2 seconds apart to about 60 seconds apart.

13. The method of claim 4, further comprising:
revising the indication provided to the user to correspond to a difference between the magnitude of the mechanical response at a third time and the magnitude of the mechanical response at the first time, and wherein the difference is indicative of a change in the health of the nerve from the first time to the third time.

* * * * *